(12) United States Patent
Doubler et al.

(10) Patent No.: US 6,440,171 B1
(45) Date of Patent: Aug. 27, 2002

(54) DOUBLE D KEY LOCKING PROSTHESIS

(75) Inventors: Robert L. Doubler, Ida, MI (US); John E. Hammill, Rossford, OH (US)

(73) Assignee: Hammill Manuf. Co., Toledo, OH (US)

(*) Notice: Subject to any disclaimer, the term of this patent is extended or adjusted under 35 U.S.C. 154(b) by 0 days.

(21) Appl. No.: 09/795,611

(22) Filed: Feb. 27, 2001

(51) Int. Cl.[7] .................................................. A61F 2/30
(52) U.S. Cl. .................................................. 623/22.42
(58) Field of Search ........................... 623/20.14, 20.15, 623/20.32, 20.34, 20.35, 22.11, 22.4, 22.41, 22.42, 22.44, 22.45, 22.46, 23.15, 23.23, 23.18

(56) References Cited

U.S. PATENT DOCUMENTS

| | | |
|---|---|---|
| 3,806,957 A | 4/1974 | Shersher |
| 5,002,578 A | 3/1991 | Luman |
| 5,026,399 A | 6/1991 | Engelbrecht et al. |
| 5,030,238 A | 7/1991 | Nieder et al. |
| 5,506,644 A | 4/1996 | Suzuki et al. |
| 5,653,765 A | 8/1997 | McTighe |
| 5,876,459 A | 3/1999 | Powell |

Primary Examiner—David J. Isabella
(74) Attorney, Agent, or Firm—McHale & Slavin PA

(57) ABSTRACT

A modular prosthesis has an intramedullary rod element which is to be inserted in a bone. The rod has a shaped proximal portion which is telescoped into one end of a bore in the trochanter element. The mating surfaces of the shaped rod and the trochanter bore form a rotationally immovable connection. A neck element is telescoped into the other end of the trochanter bore. The neck and the trochanter have mating surfaces with mating recesses. A key lock element is inserted into the mating recesses to prevent rotational movement between the neck and the trochanter. All the elements are secured together by a bolt through the neck, trochanter and rod.

10 Claims, 4 Drawing Sheets

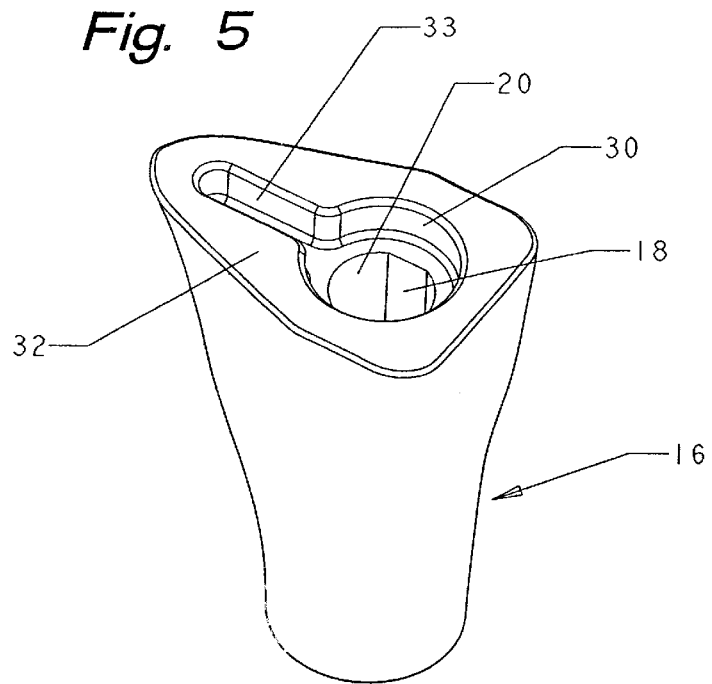
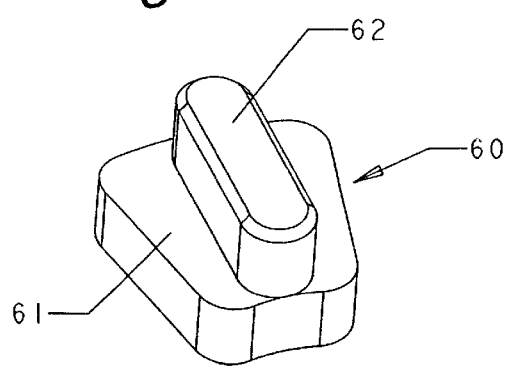
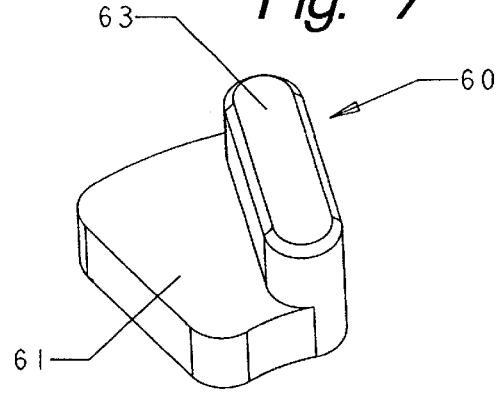

DOUBLE D KEY LOCKING PROSTHESIS

This application is related to U.S. application Ser. No. 09/527,180, filed Mar. 17, 2000 now U.S. Pat. No. 6,299, 648.

FIELD OF THE INVENTION

This invention relates to the medical field of orthopaedics and joint replacement, in particular. Modular artificial joints have several components that must be assembled and placed in the patient to reconstruct a joint. While modular joints provide the ability to custom fit an artificial joint to a patient's anatomy, the connection between the components must be without relative movement after implantation. This invention is directed to a modular artificial joint construction which provides a locking mechanism to secure the components immovably together.

BACKGROUND OF THE INVENTION

In replacing a hip joint, the head of the femur is removed along with the ball. The trochanter portion of the femur is shaped and prepared for receiving the prosthesis so that the artificial joint will closely approximate the natural hip.

Earlier artificial hip joints were made of one-piece construction requiring a large inventory of prosthesis to accommodate the various sized patients. The modular artificial joint has two or three or more elements which replace the natural hip. By manufacturing these components with interchangeable connections but different external sizes, inventories may be smaller because of the ability to mix and match components. Also, the modular prosthesis provides more flexibility in customizing the various components of a joint to the various parts of a patient's natural joint.

In a three piece artificial hip joint, the various sized components of the joint that may be selected are the intramedullary rod, the trochanter and the neck. The intramedullary rod is inserted into the end of the femur. The rod acts as a stabilizer in maintaining the artificial joint in the axis of the femur. The upper portion of the rod which extends out of the femur is fitted into a trochanter element which is shaped like the removed broad head of the femur which it replaces. This element, along with the rod, is used to adjust the length of the prosthesis to approximate the natural length of the femur.

The natural trochanter is the broadened area offset from the end of the femur. The natural trochanter may be at any radial angle about the axis of the femur. This natural angular relationship must be reproduced by the intramedullary rod and the artificial trochanter. The artificial trochanter is seated on the end of the patient's femur and is the main load bearing element of the prosthesis. It is important that this load, which is mostly compression, is transmitted along the axis of the femur.

A neck element is inserted into the trochanter element and carries an extension onto which the ball joint will be fixed. The horizontal angle between the trochanter and the neck extension is variable to reproduce the anteversion angle of the patient's natural joint. The neck carries cantilevered forces in torque and compression between the acetabulum and the trochanter. It is also important that these forces do not result in relative movement between the trochanter and the neck.

All these elements have a central bore and are permanently secured together by a bolt which is inserted into the neck element, extends through the trochanter element, and is threaded into the upper end of the rod. In some cases, the intramedullary rod may be attached to the bone with bone cement while, in other cases the cement is omitted.

When the cement is omitted, the placement and fixation of the intramedullary rod becomes more critical to pain free usage of the prosthesis. Further, it is most important that the intramedullary rod not be disturbed after insertion since this would corrupt the union between the rod and the interior of the femur.

In order to maintain the original union between the femur and the intramedullary rod, modular prosthesis have been developed to allow rotational adjustment of the several parts or elements about the rod during the placement of the prosthesis to more closely reproduce the natural structure of the hip. The modular concept also allows the selection of different sized elements, before or during surgery, to more closely approximate the natural joint.

With the advantage of flexibility gained by modular prosthesis, there comes the requirement that there be no movement between the several parts or elements after implantation. These movements may cause misalignment of the joint resulting in increased pain, trauma to the joint and, even, dislocation of the joint.

DESCRIPTION OF THE PRIOR ART

The prior art is replete with artificial prosthesis and hip joints, in particular.

Illustrative of the state of the art are U.S. Pat. No. 5,876,459 and U.S. Pat. No. 5,506,644 to Powell which disclose modular hip joints having a stem, one end of which is inserted in the intramedullary canal. The other end of the stem is tapered to fit within a second, neck, element. The neck ultimately supports the ball joint. A sleeve element is placed over the junction of the first two elements. All three elements are rotationally movable relative to each other. A bolt is driven through the bore of the neck and stem deforming a portion of the interconnected elements for a friction fit between the neck and the stem. These prior art patents disclose that the sleeve may have a polygonal shaped bore with the articulating elements having corresponding shaped portions. The interconnected elements of these hip joints do not form a static lock between each other but require a deformation of one or more elements before a friction fit is established. The deformation and friction fit is between the stem and the neck rather than the sleeve and the stem.

U.S. Pat. No. 5,653,765, to McTighe et al discloses a modular hip joint with a stem, an intermediate shoulder portion, and a proximal shoulder piece which attaches to the ball. The stem and the intermediate shoulder portion have interengaging teeth on the corresponding ends of each by which they are connected. This end-to-end connection allows for rotational movement of the elements relative to each other. The proximal shoulder piece and the intermediate shoulder piece also have an end-to-end toothed connection for rotational adjustment. This construction has two movable end-to-end connections which provide good flexibility for rotation of the elements but have small surface areas of fixation to each other limited to the surfaces of the interengaged teeth.

SUMMARY OF THE INVENTION

In the instant invention a modular prosthesis is taught which has an intramedullary rod element which is to be inserted in a bone. The rod has a shaped proximal portion which is telescoped into one end of a bore in the trochanter element. The mating surfaces of the shaped rod and the trochanter bore form a rotationally immovable connection. A neck element is telescoped into the other end of the trochanter bore permitting rotational adjustment. All the elements are locked together by a bolt through the neck and rod.

In a particularly preferred embodiment of the instant invention a modular prosthesis is described for use as a hip replacement having an intramedullary rod, a trochanter and a neck. The intramedullary rod has a distal end adapted for insertion into the intramedullary canal of the femur and a proximal end. The proximal end has a reduced radius and a circumference with opposite planar surfaces joined by curved surfaces. The proximal end includes a screw threaded blind bore along the longitudinal axis of the intramedullary rod. When the intramedullary rod is driven into the femur, it is important to align the planar surfaces of the proximal end of the rod to result in the orientation of the artificial trochanter as closely as possible to the original orientation of the natural trochanter.

The trochanter has a narrow distal end and a larger proximal end forming an external shape approximating the natural trochanter. The artificial trochanter has a through bore from the distal end to the proximal end, with the proximal end of the through bore having a smooth circumference. The proximal end of the through bore has a radial extension for receiving the tang of a key lock. The distal end of the through bore has a circumference with opposite planar sides joined by curved surfaces. The circumference of the trochanter bore and the circumference of the proximal end of the intramedullary rod telescope together with the opposite planar surfaces in intimate contact with each other forming a rotationally secure connection with the artificial trochanter approximating the position of the natural trochanter.

The neck has a planar distal end with a through bore. There is a cylindrical extension about the through bore adapted to be inserted into the proximal end of the through bore of said trochanter. Adjacent the cylindrical extension, in the planar surface, is a recess shaped to accommodate the base of a key lock. The through bore extension of the neck and the proximal end of the through bore in the trochanter telescope together forming a rotationally adjustable connection held in place by different angled key locks.

The proximal end of the through bore in the neck has an enlarged countersunk bore and the distal end of the through bore telescopes over the proximal end of the intramedullary rod. A screw threaded bolt is disposed in the countersunk bore and threadably engaged with the screw threads in said proximal end of said intramedullary rod forming a locked integral prosthesis.

Accordingly, it is an objective of the instant invention to provide a hip joint with an intramedullary rod element which is connected with the trochanter element in such a manner as to prevent any rotational movement between the elements. Rotational movement, in this context, refers to the turning of either element in a plane normal to the common longitudinal axis of the elements.

It is a further objective of the instant invention to provide a connection between the trochanter element and the intramedullary rod in such a manner as to limit the combined length of the elements.

It is a further objective of the instant invention to provide the trochanter and the neck with a locking mechanism to rigidly secure the components together to prevent relative rotation.

It is a still further objective of the invention provide a locking mechanism between the neck element and the trochanter element that permits rotational adjustment of the anteversion angle.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 5 shows a prospective of the proximal end of the trochanter with the key slot;

FIG. 6 shows a perspective of the key with a neutral orientation; and

FIG. 7 shows a prospective of the key with a anteversion of approximately +12 degrees.

DETAILED DESCRIPTION OF THE INVENTION

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Figure 1:
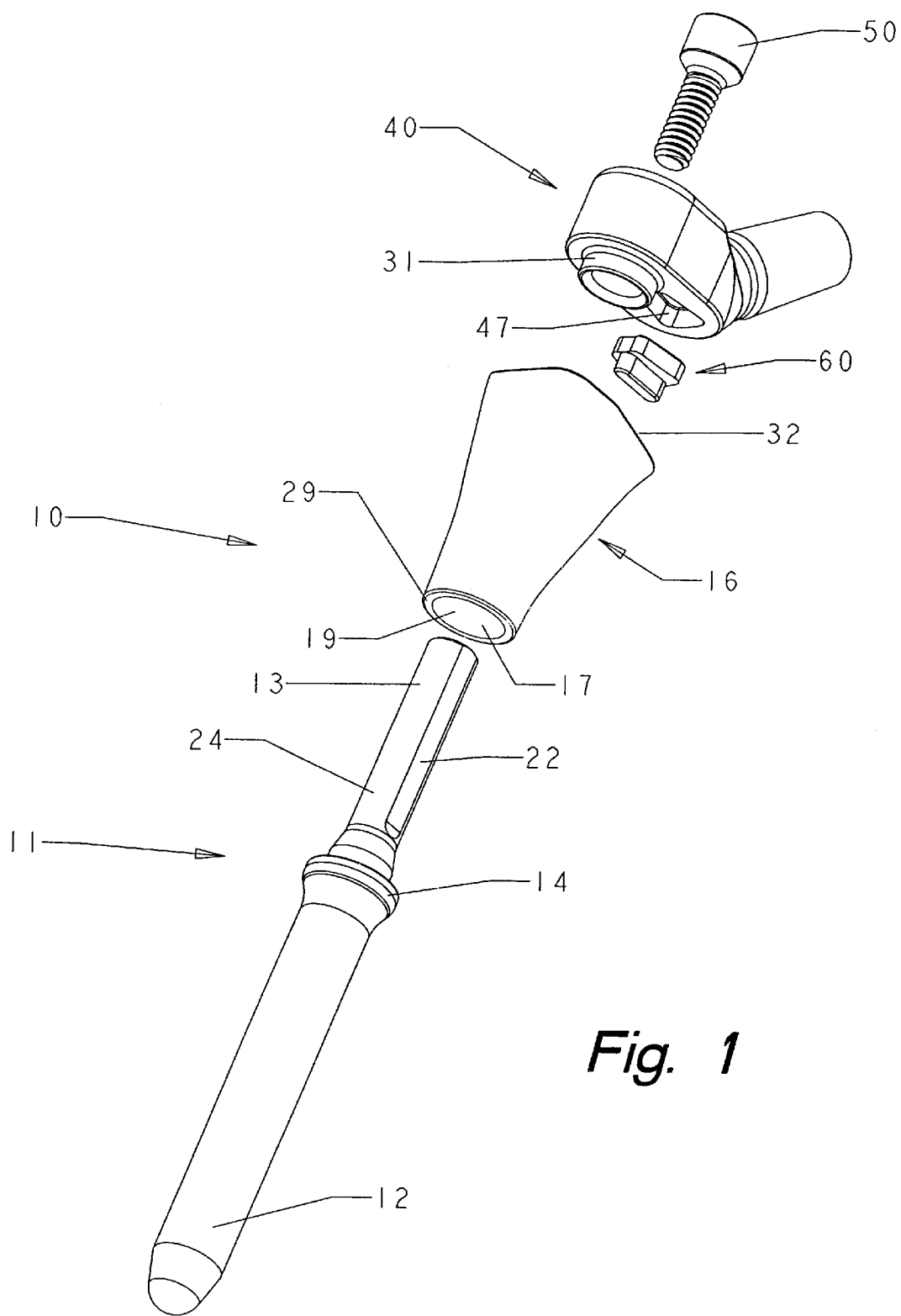
FIG. 1 is an exploded perspective of the prosthesis of this invention.

The prosthesis 10, shown in FIG. 1, has an intramedullary rod 11 which provides stability. The rod has a distal end 12 and a proximal end 13. The proximal end of the rod is smaller in diameter than the distal end. The distal end 12 is inserted into the patient's femur and forms the stabilizing connection for maintaining the prosthesis in alignment with the axis of the femur. The distal end of the rod may have flutes (not shown) to increase the surface area of the junction between the rod and the intramedullary canal of the femur. The distal end of the rod may also have a slot (not shown) along the longitudinal axis of the rod to better accommodate the internal anomalies occurring in the interior of the intramedullary canal. This structure allows the distal end of the rod to compress to a smaller diameter to more easily reach the desired depth of insertion.

Figure 2:
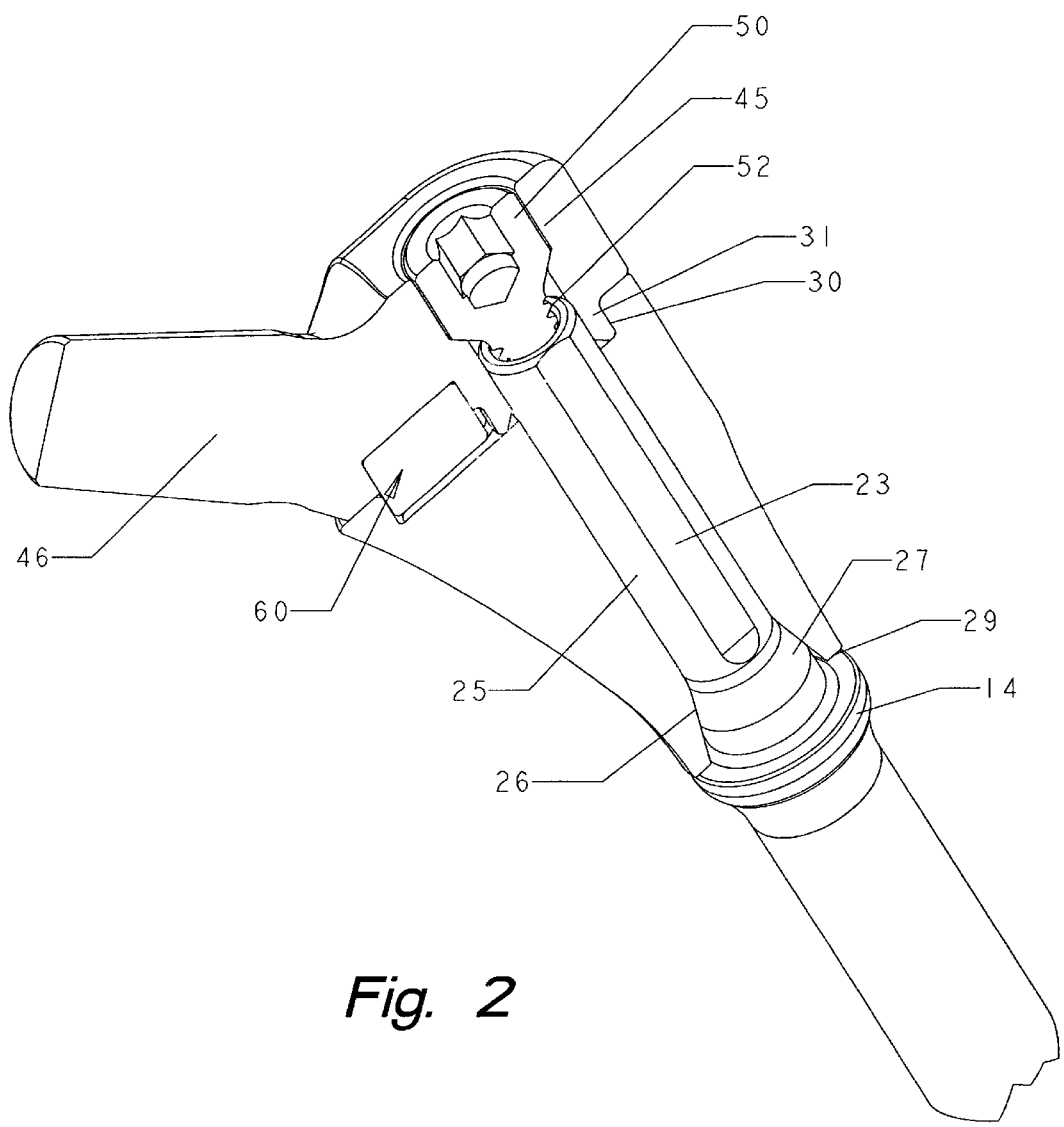
FIG. 2 shows an partial cross section of the assembled trochanter and neck of the prosthesis.

The trochanter element 16 is mounted on the proximal end of the intramedullary rod. The trochanter has a through bore portion 17 in the distal end thereof through which the proximal end 13 of the intramedullary rod is inserted. As shown in FIG. 2, the through bore portion 17 and the proximal end 13 of the intramedullary rod have corresponding mating surfaces which lock the elements together preventing any rotational movement. The bore portion 17 has planar opposite sides 18 and 19 and curved surfaces 20 and 21 joining the ends of the planar sides. The proximal end of the intramedullary rod is sized to closely fit within the bore portion 17. The proximal end of the intramedullary rod also has opposite planar sides 22 and 23 joined by curved surfaces 24 and 25.

Because the intramedullary rod 11 and trochanter 16 do not move rotationally, it is very important that the orientation of the proximal end of the rod be established during insertion of the rod into the femur. Intramedullary rod 11 provides stability and the trochanter 16 acts as the load bearing element. As mentioned earlier, these components may be provided in different lengths and diameters. The proper insertion of the rod allows the immovable connection of the trochanter to the intramedullary rod in the approximate original position of the excised head of the femur.

In addition to or in place of the complementary surfaces in bore 17 and the proximal end 13 of the intramedullary rod, the bore portion 17 may be formed with a taper 26 which is smaller toward the proximal end of the trochanter and larger at the distal end. The proximal end of the intramedullary rod may be formed with a slightly larger diameter taper 27 having a smaller end toward the proximal end. As the two elements are telescoped together, the tapered walls engage each other further strengthening the connection between the elements. In the embodiment shown in FIGS. 1 and 2, the intramedullary rod has a shoulder 14 engaging the distal circumference of the trochanter 16 for additional support. This additional support is desired when the trochanter 16 is formed of an interconnecting cellular structure to promote bone ingrowth.

Either the cooperating tapers 26 and 27 or the shoulder 14 and seating face 29 establish a precise limit to the distance the trochanter may be telescoped over the intramedullary rod. This limit, in turn, establishes the overall length of the two elements.

The proximate end of the intramedullary rod has a threaded bore 52 for receiving the threaded end of bolt 50.

The proximal end of trochanter 16 has a counter bore portion 30 which has a greater diameter than the diameter of the through bore portion 17 in the distal end. Counter bore portion 30 receives the distal end 31 of the neck element 40. This counter bore portion 30 may be cylindrical or conical. If conical, the walls of the counter bore portion 30 taper from a large diameter proximal end toward the distal end.

The counter bore portion 30 establishes a rotationally adjustable connection with the neck 40. This telescoped connection permits the prosthesis to be adjusted, after the intramedullary rod has been inserted into the femur, to approximate the natural location of the original ball. The horizontal angle between the neck and the trochanter is the anteversion angle a, shown in FIG. 4, approximately 8 degrees.

Figure 4:
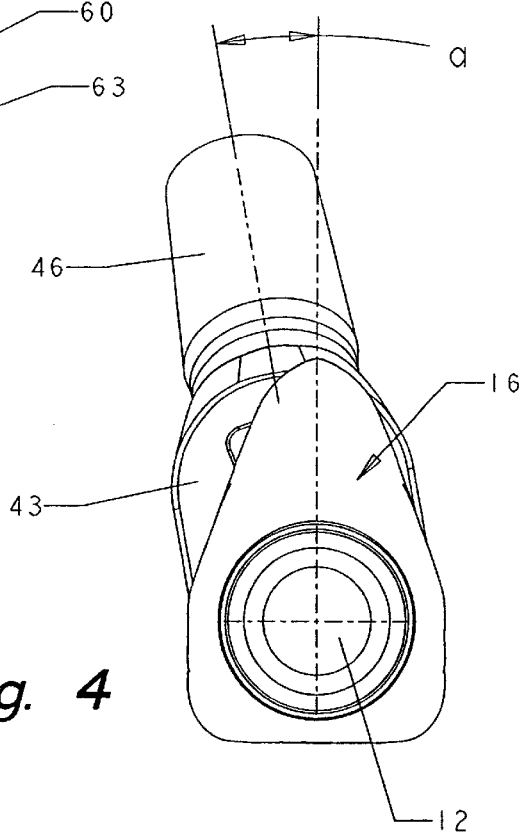
FIG. 4 shows a perspective of the proximal end of the prosthesis of this invention with the anteversion angle approximately eight (8) degrees.

The trochanter is shaped like the natural femur head and has an outer diameter that is larger than the intramedullary rod at the distal end. The distal end of the trochanter is inserted into the intramedullary canal. This junction of the trochanter and the shaft of the femur is the primary load carrying connection between the prosthesis and the patient's body. The trochanter flares to a larger diameter proximal end which has a planar surface 32 containing the counter bore portion 30. As shown in FIG. 5, the bore 30 includes a linear portion forming a recess or diametrical extension 33. The recess or bore extension 33 receives the tang 61 of the key lock 60 to establish the anteversion angle between the trochanter and the neck. As shown in FIG. 4, the anteversion angle a is neutral representing the most common angular relationship between the trochanter and the neck. As shown in FIG. 5, the bore extension 33 is formed as an extension of the counter bore 30, however the recess 33 may be separated from the bore.

The neck 40 has a partially cylindrical body 41 with a laterally extending arm 46 extending from the proximal surface of the body 41. This arm 46 carries the ball joint (not shown) for an artificial hip and can be specifically set at different anteversion angles to the trochanter and thus the axis of the femur with the key lock 60.

Figure 3:
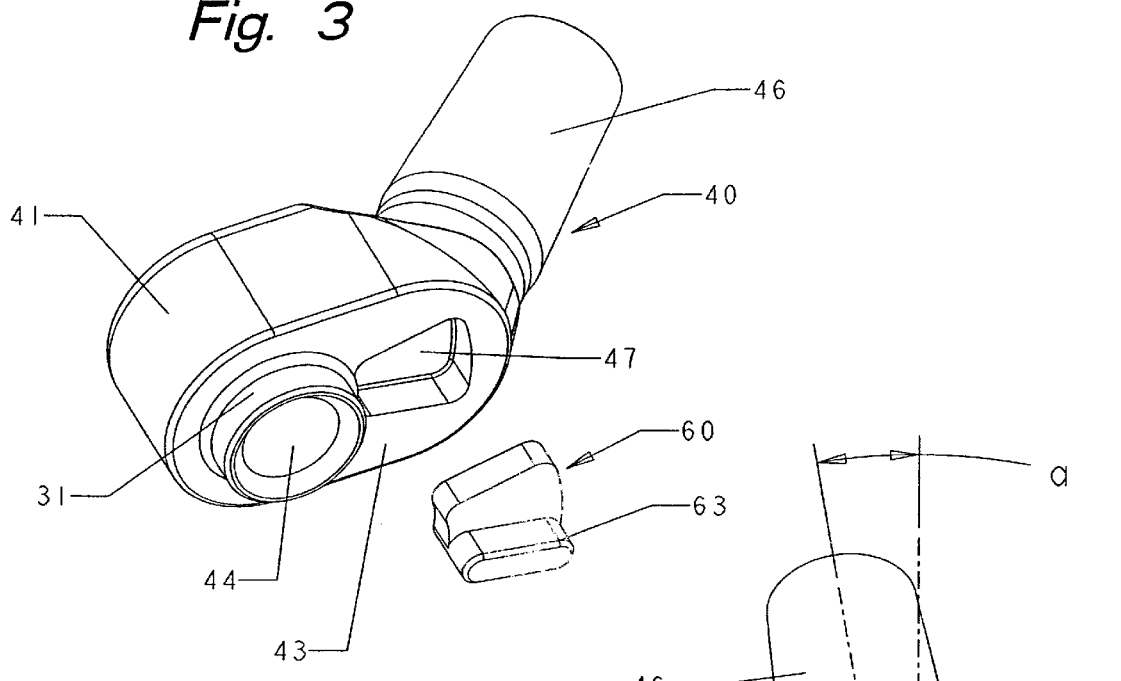
FIG. 3 is a perspective view of the distal end of the neck and the locking key of the prosthesis of this invention.

The distal surface of the neck is formed as a flat surface 43 with a depending smaller diameter distal end 31. The flat surface 43 is in intimate contact with the surface 32 of the trochanter, as shown in FIG. 2. A recess or blind bore 47 is formed in the surface 43. The recess has a geometrical shape which prevents movement of an inserted key. In FIGS. 1 and 3 the geometrical shape is illustrated as triangular but other shapes are possible.

A key lock 60 having the same peripheral configuration as the recess is placed in the recess 47. The key lock 60 has a base 61 with a thickness equivalent to or less than the depth of the recess 47. A tang 62 is formed on the base 61. The tang 62 is shaped to closely fit into the linear extension 33 in the trochanter 16. The tang has a height approximately the same as the depth of the extension 33.

The drawings illustrate one embodiment of the invention in which the base of the key lock cooperates with the blind bore in the neck and the tang cooperates with the recess in the trochanter to stop rotation. However, this organization can be reversed with the base of the key lock cooperating with the trochanter and the tang with the neck.

As shown in FIGS. 6 and 7, the tangs 62 and 63 may be located on the base at different angular orientations. In FIG. 6, a neutral orientation of the tang 62 is depicted. In FIG. 7, the tang 63 is disposed at approximately +12 degrees rotation (right) from neutral. To provide a suitable anteversion angle range of key locks, a preferred set of key locks has each tang set at one degree (1) increments, both +(right) and −(left) from neutral, resulting in a complete set of twenty five (25) key locks.

The distal end 31 is telescoped into the counter bore portion 30 of the trochanter. The outer surface of the distal end may be cylindrical or conical. The conical surface of the distal end 31 tapers from a smaller distal end toward the surface 43. The base of the conical pin is slightly larger than the through bore portion 30 so that a friction fit is established when the elements are telescoped together. This maintains the rotational axis relationship between the elements.

The neck has a bore 44 extending from the proximal end through the distal end 31. The proximal end 45 of the bore 44 is countersunk to receive the head of the bolt 50. The distal end of bore 44 receives the proximal end 13 of the intramedullary rod 11.

The prosthesis is assembled by turning the threads of the bolt 50 into the threads 52 of the intramedullary rod. As these cooperating screw threads tighten, the elements of the prosthesis are drawn together forcing the tapered distal end of the neck into a friction fit with the tapered bore of the trochanter and the trochanter to a stop limit with the intramedullary rod. In the final disposition, the trochanter and the intramedullary rod a locked together over a major part of the length of each. And the neck is locked to the rotationally immovable trochanter at a specific anteversion angle by the key lock.

The various elements or components of the prosthesis may be made in different external sizes so that a range of elements is available to meet the size needs of various patients. However, the interconnecting portions of the different sized components are of the same size or, at least, made in a range of sizes so that the different external sized elements may be securely connected as described above.

What is claimed is:

1. A modular prosthesis to be used in hip replacement comprising:

an intramedullary rod having a distal end adapted for insertion into the intramedullary canal of the femur and a tapered proximal end, said tapered proximal end having a smaller circumference than said distal end, said tapered proximal end having the smallest circumference at said proximal end, said proximal end having a screw threaded blind bore along a longitudinal axis of said intramedullary rod, a trochanter having a narrow distal end and a larger proximal end with a shaped through bore from said distal end to said proximal end, said circumference of said trochanter bore and said circumference of said proximal end of said intramedullary rod adapted to telescope together forming a rotationally secure connection, said larger proximal end of said trochanter having a recess, a neck having an extension on the distal end adapted to be inserted into the proximal end of said through bore of said trochanter, said distal end of said neck having a planar surface including a blind bore, said extension on said distal end of said neck and said proximal end of said through bore in said trochanter adapted to telescope together to form a rotationally adjustable connection, a key lock adapted to be inserted in said recess in said trochanter and said blind bore in said neck to fix said rotationally adjustable connection, said neck having a through bore, said proximal end of said through bore having a countersunk bore, said distal end of said through bore formed as said extension and adapted to telescope over the proximal end of said intramedullary rod, and a screw threaded bolt adapted to be disposed in said countersunk bore and threadably engaged with said screw threads in said proximal end of said intramedullary rod forming a locked integral prosthesis.

2. A modular prosthesis as claimed in claim 1 wherein said proximal end of said intramedullary rod has opposite planar surfaces connected by curved surfaces, said through bore of said trochanter having opposite planar surfaces connected by curved surfaces, said proximal end of said intramedullary rod and said through bore of said trochanter adapted to be telescoped together with said planar surfaces in intimate contact with each other.

3. A modular prosthesis as claimed in claim 1 wherein said intramedullary rod has a circumferential shoulder, said trochanter has a circumferential seating face, said shoulder and said seating face forming a stop limit when said intramedullary rod and said trochanter are telescoped together.

4. A modular prosthesis as claimed in claim 1 wherein said distal end of said through bore in said trochanter has a tapered surface and said proximal end of said intramedullary rod has a tapered surface, said tapered surfaces forming a stop limit when said intramedullary rod and said trochanter are telescoped together.

5. A modular prosthesis as claimed in claim 4 wherein said distal end of said neck and said proximal end of said through bore in said trochanter each have complementary tapered surfaces, said complementary tapered surfaces forming a secure connection between said neck and said trochanter when said bolt is disposed in said proximal end of said intramedullary rod.

6. A modular prosthesis as claimed in claim 1 wherein said distal end of said neck and said proximal end of said through bore in said trochanter each have complementary tapered surfaces forming a secure connection between said neck and said trochanter when said bolt is disposed in said proximal end of said intramedullary rod.

7. A modular hip prosthesis kit comprising a plurality of different sized intramedullary rods, trochanters, necks, various angled key locks, and bolts, said plurality of intramedullary rods, trochanters, necks, various angled key locks and bolts being adapted for interchangeable assembly to form a particular hip prosthesis with specific characteristics, said specific characteristics including a longitudinal axis and an anteversion angle, said angle fixed by selection of one of said various angled key locks, said one of said various angled key locks adapted to secure one of said plurality of trochanters with one of said plurality of necks in a specific horizontal angle.

8. A modular hip prosthesis kit of claim 7 wherein each of said intramedullary rods have a distal end adapted for insertion in the femur and a proximal end of reduced diameter having a screw threaded bore, each of said trochanters have an enlarged proximal end and a smaller distal end with a through bore, said through bore adapted for telescoping connection with said proximal end of any one of said intramedullary rods, said enlarged proximal end of said trochanter having a recess, each of said necks having a proximal end carrying an arm and a distal end with an extension and a blind bore, each of said necks having a through bore, one end of said through bore housed in said extension, said extension adapted to telescope into said through bore at said proximal end of any of said trochanters, said various angled key locks including a base and a tang fixed at a specific horizontal angle to said longitudinal axis of said prosthesis, each of said tangs of said key locks having a different horizontal angle, and each screw threaded bolt is adapted to be placed in the through bore of said neck, and extend through the through bore of said trochanter and be threaded into the threaded bore of said intramedullary rod to form a specific prosthesis.

9. A modular hip prosthesis kit of claim 8 wherein said intramedullary rods have a circumferential shoulder about said distal end, said trochanters have a seating face located on said distal ends, said shoulder adapted to engage said seating face for added support.

10. A modular hip prosthesis kit of claim 9 wherein said through bores of said trochanters have opposite planar surfaces joined by curved surfaces, said proximal ends of said intramedullary rods have opposite planar surfaces joined by curved surfaces, said trochanters adapted to telescope over said intramedullary rods placing said planar surfaces in intimate contact with each other and providing a rotationally secure connection.

* * * * *